(12) United States Patent
Yasuji et al.

(10) Patent No.: US 9,198,904 B2
(45) Date of Patent: Dec. 1, 2015

(54) PHARMACEUTICAL COMPOSITION FOR ORAL ADMINISTRATION

(75) Inventors: Takehiko Yasuji, Tokyo (JP); Noriyuki Kinoshita, Tokyo (JP); Hiroyuki Yoshino, Tokyo (JP); Shuuya Kawahama, Tokyo (JP); Kazuhiro Sako, Tokyo (JP); Akio Sugihara, Shizuoka (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 12/698,566

(22) Filed: Feb. 2, 2010

(65) Prior Publication Data

US 2010/0233260 A1 Sep. 16, 2010

Related U.S. Application Data

(60) Provisional application No. 61/149,854, filed on Feb. 4, 2009.

(51) Int. Cl.
| | |
|---|---|
| *A61K 31/47* | (2006.01) |
| *A61K 9/22* | (2006.01) |
| *A61P 13/02* | (2006.01) |
| *A61K 9/20* | (2006.01) |
| *A61K 9/48* | (2006.01) |
| *A61K 31/18* | (2006.01) |
| *A61K 31/439* | (2006.01) |

(52) U.S. Cl.
CPC .............. *A61K 31/47* (2013.01); *A61K 9/2086* (2013.01); *A61K 9/4866* (2013.01); *A61K 31/18* (2013.01); *A61K 31/439* (2013.01)

(58) Field of Classification Search
None
See application file for complete search history.

(56) References Cited

U.S. PATENT DOCUMENTS

| | | | |
|---|---|---|---|
| 4,373,106 A | 2/1983 | Imai et al. | |
| 4,558,156 A | 12/1985 | Imai et al. | |
| 4,703,063 A | 10/1987 | Imai et al. | |
| 4,731,478 A | 3/1988 | Niigata et al. | |
| 4,761,500 A | 8/1988 | Niigata et al. | |
| 4,868,216 A | 9/1989 | Imai et al. | |
| 4,987,152 A | 1/1991 | Imai et al. | |
| 5,391,825 A | 2/1995 | Niigata et al. | |
| 5,447,958 A | 9/1995 | Niigata et al. | |
| 6,017,927 A | 1/2000 | Takeuchi et al. | |
| 6,436,441 B1 | 8/2002 | Sako et al. | |
| 6,699,503 B1 | 3/2004 | Sako et al. | |
| 6,746,692 B2 * | 6/2004 | Conley et al. ................. 424/468 |
| 7,442,387 B2 | 10/2008 | Sugihara et al. | |
| 2003/0130338 A1 | 7/2003 | Colli et al. | |
| 2003/0203024 A1 | 10/2003 | Sako et al. | |
| 2004/0213845 A1 | 10/2004 | Sugihara et al. | |
| 2005/0100603 A1 | 5/2005 | Sako et al. | |
| 2005/0142187 A1 * | 6/2005 | Treacy et al. ................. 424/451 |
| 2006/0035923 A1 | 2/2006 | Van Meeteren et al. | |
| 2007/0231399 A1 * | 10/2007 | Kasashima et al. ........... 424/494 |
| 2007/0270459 A1 | 11/2007 | Van Meeteren et al. | |
| 2009/0035372 A1 | 2/2009 | Sugihara et al. | |
| 2009/0131469 A1 | 5/2009 | Ikeda et al. | |
| 2010/0331361 A1 * | 12/2010 | Kakizaki et al. .............. 514/305 |

FOREIGN PATENT DOCUMENTS

| | | | |
|---|---|---|---|
| EA | 007156 B1 | 8/2006 | |
| EP | 1 523 994 A1 | 4/2005 | |
| EP | 1552825 A1 * | 7/2005 | ............. A61K 31/18 |
| EP | 1 568 361 A2 | 8/2005 | |
| EP | 1852117 A1 * | 7/2007 | ........... A61K 31/439 |
| EP | 1 832 288 A1 | 9/2007 | |
| EP | 2172201 A1 | 7/2010 | |
| JP | 56-110665 | 9/1981 | |
| JP | 2004 175796 | 6/2004 | |
| WO | 03/088952 A1 | 10/2003 | |
| WO | 2009/012987 A1 | 1/2009 | |
| WO | 2009/013846 A1 | 1/2009 | |

OTHER PUBLICATIONS

Dow Polyox information sheet http://www.dow.com/dowwolff/en/pdfs/326-00013.pdf.*
Rxlist Vesicare http://www.rxlist.com/vesicare-drug.htm, accessed Apr. 17, 2014, used Wayback machine Jan. 19, 2009.*
International Search Report of PCT/JP2010/051393 dated Mar. 2, 2010.
Jeong et al., "Material properties for making fast dissolving tablets by compression method," J. Mater. Chem., 2008, vol. 18, pp. 3527-3535.
Anonymous, "A Study with Combination Treatment (Tamsulosin Hydrochloride and Solifenacin Succinate) in Male Patients with LUTS/BPH," Internet Citation, http://clincaltrials.gov/ct2/show/record/NCT00510406, Jul. 31, 2007, pp. 1-4.
Supplemental European Search Report, Jul. 27, 2012, EP application No. 10738504.9, 9 pages.
Michel, et al.; The Pharmacokinetic Profile of Tamsulosin Oral Controlled Absorption System (OCAS®); European Urology Supplements 4 (2005) 15-24.
Takenaka et al.; Discovery and Development of Tamsulosin Hydrochloride, a New $\alpha_1$-Adrenoceptor Antagonist; Yakugaku Zasshi; 115(10) 773-789 (1995).

(Continued)

*Primary Examiner* — Mina Haghighatian
*Assistant Examiner* — Erin Hirt
(74) *Attorney, Agent, or Firm* — Kilpatrick Townsend & Stockton LLP

(57) ABSTRACT

The present invention relates to a pharmaceutical composition for oral administration comprising a modified release portion containing tamsulosin or a pharmaceutically acceptable salt thereof, and an immediate release portion containing solifenacin or a pharmaceutically acceptable salt thereof and a hydrophilic substance.
In the pharmaceutical composition, the dissolution rate of each drug (in particular, solifenacin contained in the immediate release portion) is similar to those of the current single drug formulations, and the maximum percentage of drag dissolution of each drug (in particular, solifenacin contained in the immediate release portion) is 90% or more. Therefore, the pharmaceutical composition is a single formulation (i.e., a combined formulation) with a bioavailability equivalent to those of the current single drug formulations.

16 Claims, 2 Drawing Sheets

(56) References Cited

OTHER PUBLICATIONS

Omnic Ocas 0.4 Prolonged Release Tablets (film-coated) CTD Module 1 Section 1-3: Product Information (Nov. 19, 2004).
Lam, et al.; Pharmacologic management of overactive bladder; Clinical Interventions in Aging; (2007) 2(3) 337-345.
Chapple et al; Randomized, double-blind placebo-and tolterodine-controlled trial of the once-daily antimuscarinic agent solifenacin in patients with symptomatic overactive bladder; BJU Int., 93, 303-310 (2004).
Insoluble Kollidon® grades; Technical Information, BASF; Sep. 2011.
Dekker "Training Workshop on Pharmaceutical Quality, GMP and Bioequivalence. Comparative Dissolution Testing and Applications," WHO, Kiev, Oct. 3-7, 2005, 34 pages.
*Pharmaceutical Excipients*, London: Pharmaceutical Press, Electronic version, 2006, publications "Mannitol" (Aug. 11, 2005) and "Maltose" (Aug. 16, 2005), 8 pages.
Russian Office Action, Aug. 26, 2014, RU application No. 2011136636/15(054497), 11 pages (English translation included).
PH Patent Application No. 1/2011/501447, Second Examination Report (Office Action), May 20, 2014, 2 pages.
EP Patent Application No. 10 738 504.9, Third Office Action, May 27, 2014, 5 pages.
Hercules Incorporated, Aqualon Division, "Aqualon Sodium Carboxymethylcellulose—Physical and Properties," 1999, pp. 1-30, XP055066985.
Verma et al., "Current Status of Drug Delivery Technologies and Future Directories," Pharmaceutical Technology On-Line, 2001, vol. 25(2), pp. 1-14, XP055119110.
Office Action, Mexico Patent Application No. MX/a/2011/008188, Jul. 9, 2014, 10 pages.
Substantive Examination Report, Jan. 30, 2015, Malaysian Patent Application No. PI2011003445, 4 pages.
Reza et al, "Comparative evaluation of plastic, hydrophobic and hydrophilic polymers as matrices for controlled-release drug delivery," J. Pharm Pharmaceut Sci, 2003, vol. 6(2), pp. 282-291.
Vesicare—Highlights of prescribing information, 2012 Astellas Pharma US, Inc., Revised Oct. 2013, 18 pages.
Final Office Action, Feb. 25, 2015, RU Application No. 2011136636, 10 pages (includes English translation).
IL Patent Application No. 214420, first Office Action (received Nov. 4, 2014), 4 pages (with English translation).
Office Action, Apr. 10, 2015, MX application No. 28517, 8 pages (includes English translation).

* cited by examiner

PHARMACEUTICAL COMPOSITION FOR ORAL ADMINISTRATION

TECHNICAL FIELD

The present invention relates to a pharmaceutical composition for oral administration comprising a modified release portion capable of controlling the release of tamsulosin, and an immediate release portion capable of rapidly releasing solifenacin.

More specifically, the present invention relates to a pharmaceutical composition for oral administration comprising the modified release portion containing tamsulosin, a hydrogel-forming polymer, and a hydrophilic base, and the immediate release portion containing solifenacin and a hydrophilic substance, in a single formulation.

BACKGROUND ART

Tamsulosin is (R)-5-(2-{[2-(2-ethoxyphenoxy)ethyl]amino}propyl)-2-methoxybenzene-1-sulfonamide of the following structural formula. This compound was first disclosed, as well as pharmaceutically acceptable salts thereof, in patent literature 1.

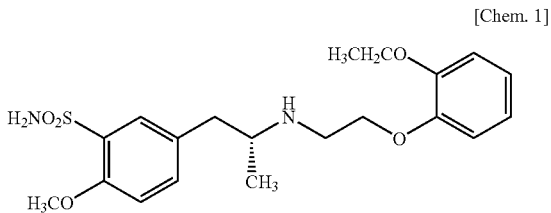

[Chem. 1]

Tamsulosin or its salts are known to have an activity of blocking adrenergic receptor $\alpha_{1A}$. In particular, tamsulosin hydrochloride has an activity of blocking $\alpha_1$ receptors in the urethra and prostate, and is widely used as an agent for treating dysuria associated with benign prostatic hyperplasia by reducing prostatic pressure in urethral pressure profile. It has been clinically confirmed that tamsulosin hydrochloride is effective in treating lower urinary tract symptoms, and thus, tamsulosin hydrochloride is an extremely useful drug in clinical use. Tamsulosin is placed on the market as Harnal (registered trademark) in Japan, Flomax (registered trademark) in the United States, and Omnic (registered trademark) in Europe.

Solifenacin is represented by the following structural formula, and its chemical name is (R)-quinuclidin-3-yl (S)-1-phenyl-1,2,3,4-tetrahydroisoquinoline-2-carboxylate.

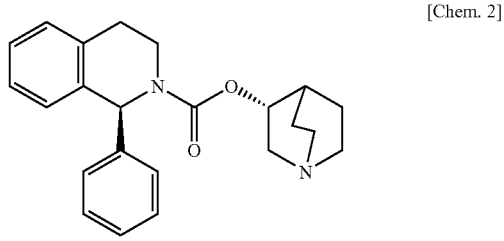 [SMILES: O=C(O[C@H]1CN2CCC1CC2)N1CCc2ccccc2[C@@H]1c1ccccc1]

[Chem. 2]

It has been reported that solifenacin or its salts have an excellent selective antagonistic activity against muscarinic $M_3$ receptors, and are useful as an agent for preventing or treating urinary diseases such as urinary incontinence and pollakiuria in neurogenic pollakiuria, neurogenic bladder, nocturnal enuresis, unstable bladder, cystospasm, and chronic cystitis; respiratory diseases such as chronic obstructive pulmonary diseases, chronic bronchitis, asthma, and rhinitis; and digestive diseases such as irritable bowel syndrome, spastic colitis, and diverticulitis (see patent literature 2).

In particular, solifenacin has high selectivity for $M_3$ receptors located in the smooth muscles, gland tissues, or the like, in comparison with $M_2$ receptors located in the heart or the like, and is useful as an $M_3$ receptor antagonist with less side effects on the heart or the like, in particular, as an agent for preventing or treating urinary incontinence and pollakiuria, chronic obstructive pulmonary diseases, chronic bronchitis, asthma, rhinitis, and the like. Solifenacin is placed on the market, as an agent for treating urinary urgency, urinary frequency, and urge incontinence in overactive bladder, as Vesicare (registered trademark) in Japan, VESIcare (registered trademark) in the United States, and Vesicare (registered trademark) in Europe.

A modified release formulation containing tamsulosin or a pharmaceutically acceptable salt is known (for example, patent literatures 3 and 4), and is placed on the market as Omnic OCAS (registered trademark).

This provides a modified release formulation with a blood drug concentration profile showing a lower peak/trough ratio than that of a conventional modified release formulation. The modified release formulation not only reduces the occurrence of side effects such as orthostatic anemia, but also is expected to increase the dose or sustain the efficacy for a long period. Further, food effects on blood drug concentrations can be avoided, and a high safety profile is expected in view of drug dosing compliance (patent literature 5).

To treat lower urinary tract symptoms associated with benign prostatic hyperplasia, a pharmaceutical composition containing tamsulosin or a pharmaceutically acceptable salt thereof and solifenacin or a pharmaceutically acceptable salt thereof, more specifically, a pharmaceutical composition for treating lower urinary tract symptoms associated with benign prostatic hyperplasia, and an invention relates to a combination use of both drugs, are disclosed (patent literature 6).

Tamsulosin or a pharmaceutically acceptable salt thereof is effective in treating voiding symptoms and, by contrast, solifenacin or a pharmaceutically acceptable salt thereof is effected in treating storage symptoms, and thus, both compounds exhibit contradictory effects. However, the combination use of both drugs unexpectedly resulted in the further amelioration of storage symptoms without the decrease in amelioration of voiding symptoms, in comparison with a single administration of each drug alone.

Because it was confirmed that the combination therapy using tamsulosin or a pharmaceutically acceptable salt thereof and solifenacin or a pharmaceutically acceptable salt thereof was clinically effective in treating lower urinary tract symptoms associated with benign prostatic hyperplasia, it is desired to provide the medical field with a combined formulation (i.e., a single formulation) containing both drugs to improve drug dosing compliance. As an embodiment of the combined formulation for efficiently exhibiting the effects obtainable by the combination use, while maintaining the decreased occurrence of side effects and the sustainment of efficacies, a combined formulation of a modified release formulation containing tamsulosin with an ordinary formulation (an immediate release formulation) containing solifenacin may be proposed. However, because the drug dissolution rates in both formulations are different from each other, even when a single formulation (i.e., the combined formulation) is prepared from both formulations, it is desired that the drug releasing rate in each formulation contained in the single formulation is not much affected.

CITATION LIST

Patent Literature

[patent literature 1] Japanese Unexamined Patent Publication (Kokai) No. 56-110665
[patent literature 2] U.S. Pat. No. 6,017,927 (corresponding to International Publication No. WO96/20194)
[patent literature 3] International Publication No. WO94/06414
[patent literature 4] International Publication No. WO2004/078212
[patent literature 5] U.S. Patent Application Publication 2005-0100603
[patent literature 6] International Publication No. WO2009/013846

SUMMARY OF INVENTION

Technical Problem

The present inventors used the same components of the current products, i.e., Vesicare (product name) with a rapid drug releasing rate (85% for 30 minutes) and modified drug release formulation Omnic OCAS (product name), to prepare a single formulation (i.e., a combined formulation) (Comparative Example 1 described below).

More specifically, bi-layered tablets consisting of a modified release portion containing tamsulosin, polyethylene oxide, polyethylene glycol, and magnesium stearate, and an immediate release portion containing solifenacin, lactose, corn starch, hydroxypropylmethylcellulose, and magnesium stearate were prepared. A dissolution test was carried out using the obtained bi-layered tablets to unexpectedly find:
[1] that the dissolution rate of solifenacin was decreased, and was less than 85% for 30 minutes, and
[2] that the maximum percentage of solifenacin dissolution was less than 90%.

When the dissolution rate or the maximum percentage of solifenacin dissolution is decreased, it is concerned that a decreased availability in the living body, i.e., bioavailability, will be caused and, as a result, pharmacological effects equivalent to those obtained by the combination use of the current formulations (single drug formulations) cannot be obtained.

An object of the present invention is to provide the medical field with a single formulation (a combined formulation) comprising a modified release portion containing tamsulosin and an immediate release portion containing solifenacin, more specifically, (1) to provide a single formulation (a combined formulation) having dissolution rates of both drugs (in particular, a dissolution rate of solifenacin in the immediate release portion) similar to those of the current single drug formulations, and (2) to provide a single formulation (a combined formulation) having maximum percentages of dissolution of both drugs (in particular, a maximum percentage of solifenacin dissolution in the immediate release portion) of 90% or more, and having a bioavailability equivalent to those of the current single drug formulations.

Solution to Problem

The above results, i.e., the delay of the dissolution rate of solifenacin from the bi-layered tablet and the decrease in the maximum percentage of solifenacin dissolution, were remarkably unexpected for the present inventors, because the solubility of solifenacin in water is 610 mg/mL, and thus, solifenacin is classified into water-soluble substances in accordance with the expression of solubility described in the Japanese Pharmacopoeia, and further, the current formulation [Vesicare (registered trademark)] has been designed as an immediate release formulation.

As a difference in the environment in the living body between an administration of the bi-layered tablet and an administration of each formulation (single drug formulation), it can be pointed out that the modified release portion is close to the immediate release portion, and thus, solifenacin dissolved from the immediate release portion exists near the modified release portion containing another drug.

In particular, it is unexpected that there is a possibility that water-"soluble" solifenacin is dissolved and incorporated into the modified release portion containing a hydrogel-forming polymer.

The disintegration times of immediate release single drug formulations, which are composed of the same components as those of mixed powders for an immediate release portion prepared in Examples 1 to 3 and Comparative Example 1 described below, respectively, are shown in FIG. 1, and the drug release times from the immediate release single drug formulations are shown in FIG. 2. When the same components (solifenacin, lactose, corn starch, hydroxypropylmethylcellulose, and magnesium stearate) as those of the current formulation shown as the mixed powder for an immediate release portion described in Comparative Example 1 in these Figures were used, this formulation exhibited rapid disintegration and rapid drug release. This result was different from that of the single formulation (combined formulation), and thus, the result of the bi-layered tablet as the single formulation (combined formulation) was remarkably unexpected.

Under these circumstances, the present inventors focused attention on the improvement of the release rate of solifenacin and the maximum percentage of solifenacin dissolution, and have conducted intensive studies, and completed the present invention.

The present invention provides:
[1] a pharmaceutical composition for oral administration comprising (1) a modified release portion comprising tamsulosin or a pharmaceutically acceptable salt thereof, and (2) an immediate release portion comprising solifenacin or a pharmaceutically acceptable salt thereof and a hydrophilic substance;
[2] the pharmaceutical composition for oral administration of [1], wherein the immediate release portion is disintegrated and/or dissolved before the modified release portion forms a gel;
[3] the pharmaceutical composition for oral administration of [1] or [2], wherein 70% or more of solifenacin is dissolved for 15 minutes;
[4] the pharmaceutical composition for oral administration of [3], wherein 90% or more of solifenacin is dissolved for 60 minutes;
[5] the pharmaceutical composition for oral administration of [4], wherein 70% or more of solifenacin is dissolved for 15 minutes and 90% or more of solifenacin is dissolved for 60 minutes;
[6] the pharmaceutical composition for oral administration of [5], wherein 85% or more of solifenacin is dissolved for 30 minutes and 90% or more of solifenacin is dissolved for 60 minutes;
[7] the pharmaceutical composition for oral administration of any one of [1] to [6], wherein the hydrophilic substance is one compound or two or more compounds selected from the group consisting of polyethylene glycol, maltose, polyvinylpyrrolidone, and mannitol;

[8] the pharmaceutical composition for oral administration of any one of [1] to [7], wherein the hydrophilic substance accounts for 5% by weight to 99% by weight;

[9] the pharmaceutical composition for oral administration of any one of [1] to [8], wherein one hydrophilic substance or two or more hydrophilic substances selected from the group consisting of polyethylene glycol, maltose, polyvinylpyrrolidone, and mannitol are used as a binder;

[10] the pharmaceutical composition for oral administration of any one of [1] to [9], wherein mannitol as the hydrophilic substance is used as a filler;

[11] the pharmaceutical composition for oral administration of any one of [1] to [10], wherein the modified release portion contains a polymer which forms a hydrogel;

[12] the pharmaceutical composition for oral administration of [11], wherein the hydrogel-forming polymer has a viscosity of 4000 mPa·s or more in a 1% aqueous solution (25° C.);

[13] the pharmaceutical composition for oral administration of [12], wherein the hydrogel-forming polymer is one polymer or two or more polymers selected from the group consisting of polyethylene oxide, hydroxypropylmethylcellulose, carboxymethylcellulose sodium, and a carboxyvinyl polymer;

[14] the pharmaceutical composition for oral administration of [13], wherein the hydrogel-forming polymer is polyethylene oxide;

[15] the pharmaceutical composition for oral administration of [14], wherein polyethylene oxide has a viscosity-average molecular weight of 5,000,000 or more;

[16] the pharmaceutical composition for oral administration of any one of [11] to [15], wherein the hydrogel-forming polymer accounts for 5% by weight to 95% by weight;

[17] the pharmaceutical composition for oral administration of any one of [1] to [16], wherein the modified release portion further contains an additive which allows water to penetrate into the formulation;

[18] the pharmaceutical composition for oral administration of [17], wherein the additive which allows water to penetrate into the formulation has a solubility such that the amount of water necessary to dissolve 1 g of the additive is 5 mL or less;

[19] the pharmaceutical composition for oral administration of [18], wherein the additive which allows water to penetrate into the formulation accounts for 3% by weight to 80% by weight;

[20] the pharmaceutical composition for oral administration of any one of [1] to [19], which is a pharmaceutical composition for treating lower urinary tract symptoms associated with benign prostatic hyperplasia; and

[21] the pharmaceutical composition for oral administration of any one of [1] to [20], wherein the pharmaceutical composition is a tablet.

Advantageous Effects of Invention

The present invention provides a pharmaceutical composition for oral administration comprising a modified release portion containing tamsulosin or a pharmaceutically acceptable salt thereof, and an immediate release portion containing solifenacin or a pharmaceutically acceptable salt thereof. The pharmaceutical composition of the present invention has a drug release similar to that of each single drug formulation, and thus, a single formulation (combined formulation) capable of expecting pharmacological effects equivalent to those of the single drug formulations can be provided. Further, it is expected to improve drug dosing compliance, because the number of the formulations to be administered is decreased.

Figure 1:
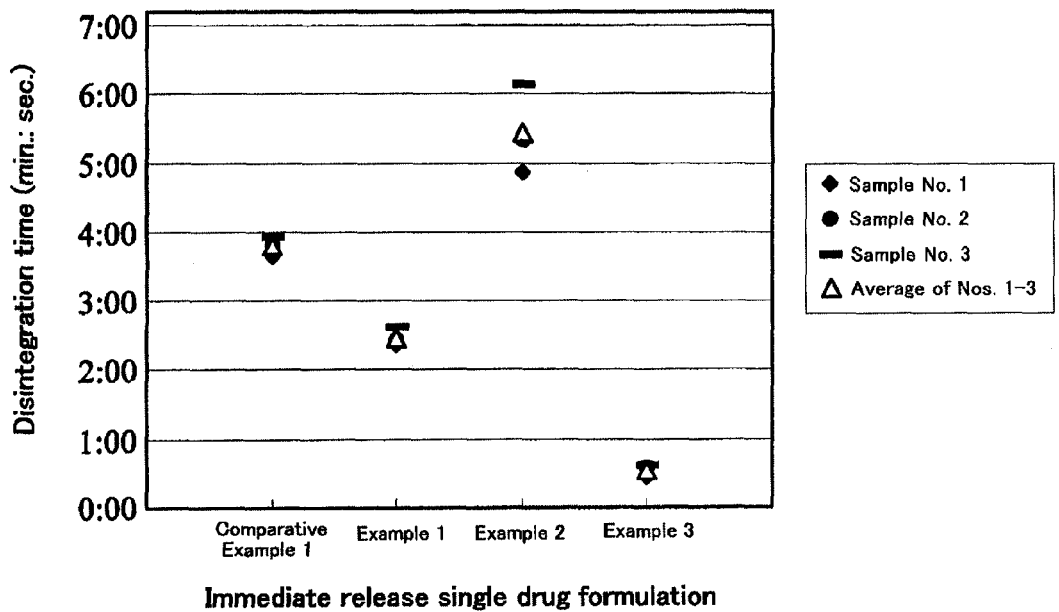
FIG. 1 is a graph showing the disintegration times of immediate release single drug formulations, which are composed of the same components as those of mixed powders for an immediate release portion prepared in Examples 1 to 3 of the present invention and Comparative Example 1, respectively.
Figure 2:
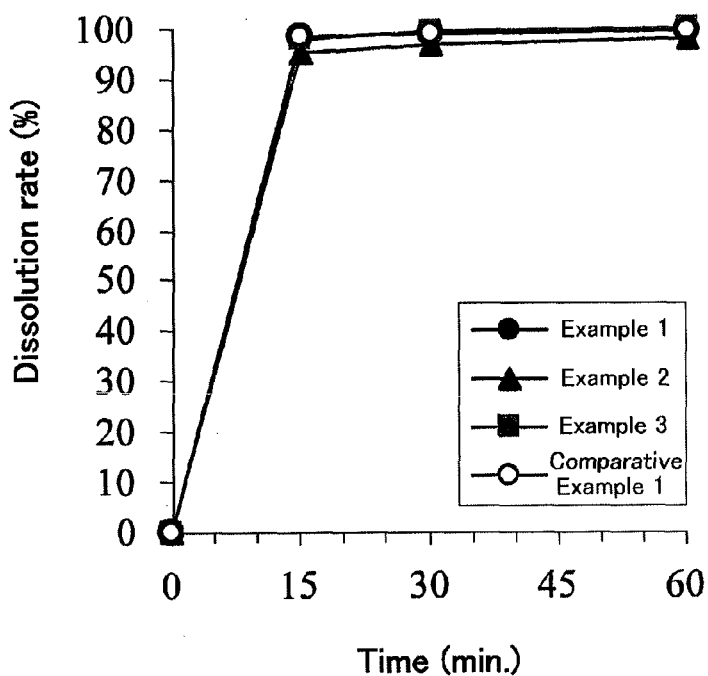
FIG. 2 is a graph showing the drug release profiles of the immediate release single drug formulations, which are composed of the same components as those of mixed powders for an immediate release portion prepared in Examples 1 to 3 of the present invention and Comparative Example 1, respectively.

With respect to the disintegration time of each immediate release single drug formulation shown in FIG. 1, and the drug release from each immediate release single drug formulation shown in FIG. 2, the immediate release single drug formulation composed of the same components as those of the mixed powder for an immediate release portion prepared in Comparative Example 1 exhibited rapid disintegration, and rapid drug release in which the dissolution was completed for 15 minutes, as well as the immediate release single drug formulations composed of the same components as those of the mixed powders for an immediate release portion prepared in Examples 1 to 3, respectively.

Figure 3:
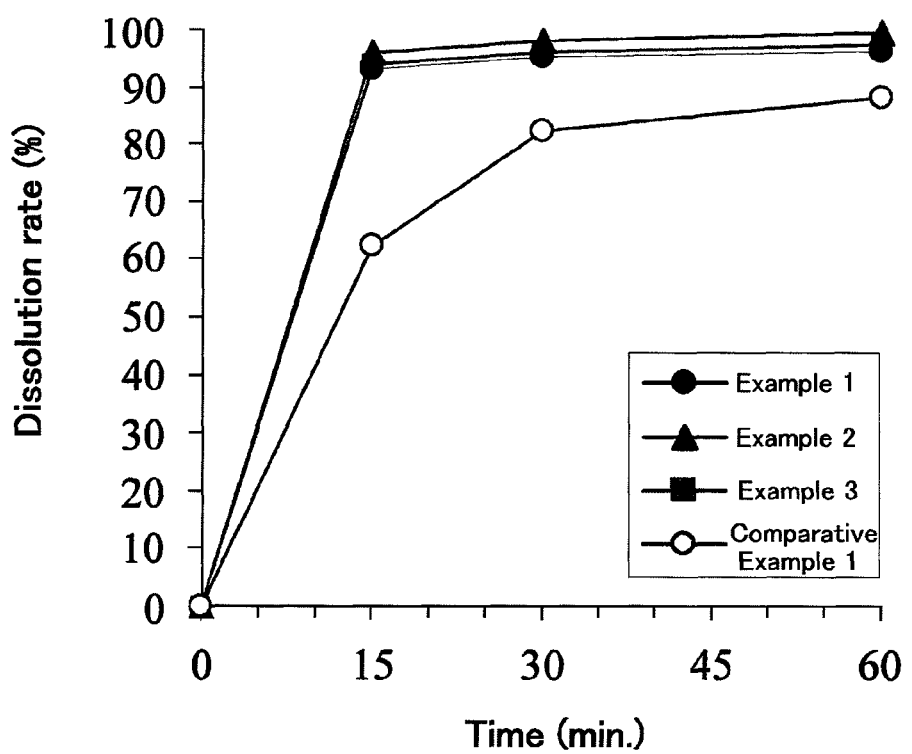
FIG. 3 is a graph showing the dissolution profiles of the pharmaceutical compositions prepared in Examples 1 to 3 of the present invention and Comparative Example 1.

With respect to the single formulations (combined formulations), as shown in FIG. 3, although the immediate release single drug formulations exhibited the same rapid disintegration and the same rapid solubility, water-soluble solifenacin was dissolved and incorporated into the modified release portion containing a hydrogel-forming polymer, in the pharmaceutical composition prepared Comparative Example 1, and surprisingly the drug release rate did not reach 90%, and the complete drug release was not observed.

DESCRIPTION OF EMBODIMENTS

Embodiments of the present invention will be explained hereinafter.

The term "single drug formulation" as used herein means an embodiment of a formulation containing a drug.

The term "combined formulation" as used herein is also referred to as "single formulation", and means an embodiment of a formulation containing two or more drugs in the formulation. The term "combined formulation" includes a formulation containing functionally different subformulations such as the modified release portion and the immediate release portion in the present invention.

The term "modified release portion" as used herein means an embodiment contained in the single formulation, and a portion which controls the release of the drug.

The term "immediate release portion" as used herein means an embodiment contained in the single formulation, and a portion which rapidly releases the drug from the pharmaceutical composition (in the case of a "soluble" drug, "release" has almost the same meanings as "dissolution").

The term "maximum percentage of dissolution" as used herein means the percentage of dissolution when a dissolution rate of the drug from the pharmaceutical composition reaches a plateau in a dissolution test under predetermined conditions.

The pharmaceutical composition for oral administration of the present invention will be explained hereinafter.

Tamsulosin or a pharmaceutically acceptable salt thereof, which may be used in the present invention, is easily available by preparing it in accordance with the methods described in JP 56-110665 and JP 62-114952, or modified methods thereof.

Tamsulosin can form pharmaceutically acceptable salts with various inorganic and organic acids. These pharmaceutically acceptable salts may be used in the present invention. Examples of the salts include salts with inorganic acids such as hydrochloric acid, sulfuric acid, and phosphoric acid; salts with organic acids such as fumaric acid, malic acid, citric acid, and succinic acid; salts with alkali metals such as sodium and potassium; and salts with alkali earth metals such as calcium and magnesium. Tamsulosin hydrochloride may be used in another embodiment. These salts can be prepared by a conventional method.

The dose of tamsulosin or a pharmaceutically acceptable salt thereof may be appropriately determined for each patient in accordance with, for example, the route of administration, symptoms of a disease, the age and the sex of a patient to be treated, or the like. When tamsulosin hydrochloride is orally administered to an adult, the daily dose is approximately 0.1 mg to 1.6 mg as the active ingredient, and is orally administered once a day.

Solifenacin or a pharmaceutically acceptable salt thereof, which may be used in the present invention, is easily available by preparing it in accordance with the method described in WO 96/20194, or a modified method thereof.

Solifenacin can forms pharmaceutically acceptable salts with various inorganic and organic acids. These pharmaceutically acceptable salts may be used in the present invention. Examples of the salts include acid addition salts with mineral acids such as hydrochloric acid, hydrobromic acid, hydriodic acid, sulfuric acid, nitric acid, and phosphoric acid; and acid addition salts with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, and glutamic acid. Solifenacin succinate may be used in another embodiment. These salts can be prepared by a conventional method.

The dose of solifenacin or a pharmaceutically acceptable salt thereof may be appropriately determined for each patient in accordance with, for example, the route of administration, symptoms of a disease, the age and the sex of a patient to be treated, or the like. When solifenacin succinate is orally administered to an adult, the daily dose is approximately 0.01 mg/kg to 100 mg/kg as the active ingredient, and is administered once or divided into two to four doses per day. Alternatively, when it is intravenously administered to an adult, the dose is 0.01 mg/kg/dose to 10 mg/kg/dose, and the dose is administered once or several times per day.

The content of each drug is not particularly limited, so long as it is an effective amount for the treatment or prevention. The content of each drug per formulation is, for example, 85% by weight or less, 80% by weight or less as another embodiment, 50% by weight or less as still another embodiment, and 10% by weight or less as still another embodiment.

The "modified release portion" in the present invention comprises tamsulosin or a pharmaceutically acceptable salt thereof, a hydrogel-forming polymer (hereinafter sometimes referred to as a polymer which forms a hydrogel), and a hydrophilic base (hereinafter sometimes referred to as an additive which allows water to penetrate into the formulation). The "modified release portion" is defined herein as a portion in which the point showing a percentage of drug dissolution of 50% from the pharmaceutical composition is from 3 hours to 15 hours from the beginning of a dissolution test, when the dissolution test is carried out in accordance with a dissolution test, method 2 (paddle method, 50 rpm to 200 rpm) described in the Japanese Pharmacopoeia, or a dissolution test carried out in accordance with a dissolution test, method 1 (basket method, 50 rpm to 200 rpm) described in the Japanese Pharmacopoeia.

The hydrogel-forming polymer, which may be used in the present invention, is not particularly limited, so long as it has properties, such as viscosity and the like at the time of gelling, that maintain the form of the almost completely gelled formulation against the motility of the digestive tract accompanied by food digestion, and migrate the gelled formulation to the colon in the lower digestive tract while maintaining the shape to a certain extent. As the hydrogel-forming polymer, a polymer having a high viscosity at the time of gelling, such as a polymer with a viscosity of 4000 mPa·s or more in a 1% aqueous solution at 25° C., may be used.

The properties of a polymer are dependent on its molecular weight, and a polymer with a higher molecular weight is preferable as the hydrogel-forming polymer, which may be used in the present invention. Examples of the polymer with a higher molecular weight include polyethylene oxide with an average molecular weight of 5,000,000 or more, an average molecular weight of 7,000,000 or more in another embodiment, an average molecular weight of 5,000,000 to 8,000,000 in still another embodiment, and an average molecular weight of 7,000,000 to 8,000,000 in still another embodiment.

Examples of the polymer include:
polyethylene oxide (PEO) [for example, product names, Polyox WSR-308 (average molecular weight: 8,000,000, viscosity: 10000-15000 mPa·s (1% aqueous solution at 25° C.)), Polyox WSR-303 (average molecular weight: 7,000,000, viscosity: 7500-10000 mPa·s (1% aqueous solution at 25° C.)), Polyox WSR Coagulant (average molecular weight: 5,000,000, viscosity: 5500-7500 mPa·s (the same as above)), each manufactured by Dow];
hydroxypropylmethylcellulose (HPMC) [for examples, product names, Metolose 90SH100000 (viscosity: 4100-5600 mPa·s (1% aqueous solution at 20° C.)), and Metolose 90SH30000 (viscosity: 25000-35000 mPa·s (2% aqueous solution at 20° C.)), each manufactured by Shin-Etsu Chemical Co., Ltd.]; carboxymethylcellulose sodium (CMC-Na) [for example, product names, Sunrose F-1000MC (average molecular weight: 420,000, viscosity: 8000-12000 mPa·s (the same as above)), and HEC DAICEL SE900 (average molecular weight: 1,560,000, viscosity: 4000-5000 mPa·s (the same as above)), manufactured by Daicel chemical Industries, Ltd.]; and carboxyvinyl polymers [for example, Carbopol 940 (average molecular weight: approximately 2,500,000), manufactured by B. F. GoodRich Chemical)]. Polyethylene oxide may be used in another embodiment.

These hydrogel-forming polymers may be used alone, or as an appropriate combination of two or more thereof. When two or more polymers having a viscosity or an average molecular weight beyond the above-mentioned specific ranges are mixed, and the resulting mixture has the same properties within the specific ranges, the mixture of the polymers is included in the hydrogel-forming polymers which may be used in the present invention.

To release a drug in the colon of a human, it is preferable that part of the gelled formulation remains in the colon after at least 6 to 8 hours, preferably 12 hours or more, from the administration of the formulation. The preparation of a hydrogel-forming formulation having such properties varies according to the size of the formulation, the kind of polymers, properties of a drug and an additive that allows water to penetrate into the formulation, the contents thereof, and the like. For a formulation of 600 mg or less per tablet, the content of the hydrogel-forming polymer with respect to the weight of the formulation is, for example, 5% by weight to 95% by weight, and preferably 10% by weight to 90% by weight in another embodiment, and the content of the hydrogel-forming polymer with respect to the weight of the modified release portion is, for example, 10% by weight to 95% by weight, and preferably 15% by weight to 90% by weight in another embodiment. The content per formulation is preferably 40 mg or more, and 60 mg or more in another embodiment. When the content is lower than these values, there is a possibility that sufficient sustained release is not achieved, due to erosion in the digestive tract for a long time.

The additive which allows water to penetrate into the formulation (also referred to as "hydrophilic base"), which may be used in the present invention, is not particular limited, so long as it is a substance capable of imparting, to the formulation, the feature which ensures penetration of water into the formulation. Examples of the hydrophilic base include a substance having a solubility such that the amount of water necessary to dissolve 1 g of the hydrophilic base at 20±5° C. is 5 mL or less, and 4 mL or less in another embodiment. When the hydrophilic base has a higher solubility to water, the effect that allows water to penetrate into the formulation is higher.

Examples of the hydrophilic base include: water-soluble polymers, such as polyethylene glycol [PEG: for example, product names PEG 400, PEG 1500, PEG 4000, PEG 6000, and PEG 20000 (manufactured by NOF Corporation)], and polyvinylpyrrolidone [PVP: for example, product name PVP K30 (manufactured by BASF)];
sugar alcohols, such as D-sorbitol and xylitol; saccharides, such as sucrose, anhydrous maltose, D-fructose, dextran (for example, Dextran 40), and glucose;
surfactants, such as polyoxyethylene polyoxypropylene glycol [for example, Pluronic F68 (manufactured by Asahi Denka and the like)];
salts, such as sodium chloride and magnesium chloride; organic acids, such as citric acid and tartaric acid; amino acids, such as glycine, (3-alanine, and lysine hydrochloride; and
aminosaccharides, such as meglumine. In another embodiment, PEG6000, PVP, D-sorbitol, or the like may be used. These hydrophilic bases may be used alone, or as an appropriate combination of two or more thereof.

The content of the hydrophilic base may vary according to various factors, such as properties (solubility, therapeutic effect, and the like) and content of a drug, solubility of the hydrophilic base, properties of the hydrogel-forming polymer, conditions of a subject to be administered, and the like, but an amount in which gelling is almost completely achieved during the retention of the formulation in the upper digestive tract is preferred. A retention time of a drug in the upper digestive tract varies according to species and individuals, but those after administration in dogs and humans are approximately 2 hours and approximately 4 to 5 hours, respectively [Br. J. Clin. Pharmac., (1988) 26, 435-443]. In humans, the content of the hydrophilic base is preferably an amount in which gelling of the formulation is almost completely achieved after 4 to 5 hours from the administration thereof.

The content is, for example, approximately 3% by weight to 80% by weight (approximately 3% by weight to 60% by weight in another embodiment) with respect to the weight of the formulation, and for example, approximately 5% by weight to 80% by weight (approximately 5% by weight to 60% by weight in another embodiment) with respect to the weight of the modified release portion.

The hydrophilic substance which forms the "immediate release portion" used in the present invention is not particularly limited, so long as the immediate release portion can be disintegrated and/or dissolved. In another embodiment, The hydrophilic substance is not particularly limited, so long as the immediate release portion can be almost completely disintegrated before the modified release portion forms a gel. The state "almost completely" can be detected or judged when the hydrophilic substance which forms the matrix of the immediate release portion is almost completely disintegrated visually under the dissolution test conditions. The state "almost completely" can be detected or judged, on the basis of the results of the dissolution test, when 70% or more of the drug (85% or more in another embodiment, and 90% or more in still another embodiment) is dissolved for 15 minutes, or when 85% or more of the drug (90% or more in another embodiment) is dissolved for 30 minutes and 90% or more of the drug is dissolved for 60 minutes. The maximum percentage of dissolution in the immediate release portion is defined by showing the percentage of drug dissolution from the pharmaceutical composition after 60 minutes under the conditions where the dissolution test is carried out in accordance with a dissolution test, method 2 (paddle method, 50 rpm to 200 rpm) described in the Japanese Pharmacopoeia, or a dissolution test carried out in accordance with a dissolution test, method 1 (basket method, 50 rpm to 200 rpm) described in the Japanese Pharmacopoeia.

Examples of the hydrophilic substance include D-mannitol, maltose, polyethylene glycol, and polyvinylpyrrolidone.

The immediate release portion comprises solifenacin or a salt thereof and the hydrophilic substance. The hydrophilic substance can has functions as a filler and/or a binder. As the filler, D-mannitol, maltose, polyethylene glycol, or polyvinylpyrrolidone may be used. As the binder, maltose, polyethylene glycol, or polyvinylpyrrolidone may be used. Examples of polyethylene glycol (PEG) include PEG 400, PEG 1500, PEG 4000, PEG 6000, and PEG 20000 (products name, each manufactured by NOF Corporation). Examples of polyvinylpyrrolidone (PVP) include Kollidon K25 and Kollidon K90 (product names, each manufactured by BASF).

With respect to the state of the hydrophilic substance which exists in the immediate release portion, the present invention includes an embodiment in which the hydrophilic substance is uniformly contained in the immediate release portion, and an embodiment in which the hydrophilic substance ununiformly exists in the interface of the immediate release portion.

The hydrophilic substances may be used alone, or as an appropriate combination of two or more thereof.

The content of the hydrophilic substance is, for example, 2% by weight to 40% by weight (4% by weight to 35% by weight in another embodiment) with respect to the formulation, and 5% by weight to 95% by weight (10% by weight to 90% by weight in another embodiment, and 20% by weight to 80% by weight in still another embodiment) with respect to the immediate release portion.

Various pharmaceutical additives may be appropriately used to prepare the pharmaceutical composition of the present invention, if desired, and are not particularly limited, so long as they are pharmaceutically and pharmacologically acceptable. Examples of the pharmaceutical additive include a binder, a stabilizer, a disintegrating agent, an acidulant, an effervescent agent, an artificial sweetener, a flavor, a lubricant, a coloring agent, a buffer, an antioxidant, and a surfactant.

Examples of the binder include gum arabic, hydroxypropylmethylcellulose, hydroxypropylcellulose, and hydroxyethylcellulose.

Examples of the stabilizer include yellow ferric oxide, red ferric oxide, and black iron oxide. The pharmaceutical composition for oral administration of the present invention preferably contains yellow ferric oxide and/or red ferric oxide as the stabilizer for polyethylene oxide. When the stabilizer is added by physical mixing in the matrix, the content of the stabilizer is, for example, 1% by weight to 20% by weight (3% by weight to 15% by weight in another embodiment) with respect to the weight of the formulation. For example, the content of red ferric oxide is, for example, 5% by weight to 20% by weight (10% by weight to 15% by weight in another embodiment) with respect to the weight of the formulation. The content of yellow ferric oxide is, for example, 1% by weight to 20% by weight (3% by weight to 10% by weight in another embodiment). When the stabilizer is coated by film coating, the content is, for example, 0.3% by weight to 2% by weight (0.5% by weight to 1.5% by weight in another embodiment) with respect to the weight of the tablet. In this case, the concentration of yellow ferric oxide or red ferric oxide contained in the film is, for example, 5% by weight to 50% by weight (10% by weight to 20% by weight in another embodiment). The term "physical mixing in the matrix" as used herein means, for example, a method in which a drug, polyethylene oxide, and the ferric oxide(s) are uniformly dispersed, and as a result, the drug and the ferric oxide are uniformly dispersed in PEO as the main base of the formulation. The term "film coating" as used herein means, for example, a method in which the ferric oxide(s) is dissolved or suspended in a water-soluble polymer solution such as hydroxypropylmethylcellulose, and tablets that have been previously prepared are coated with this solution or suspension to form a thin layer. Yellow ferric oxide and/or red ferric oxide, which may be used in the present invention, may exist at any place in the formulation. The ferric oxide(s) may be contained, for example, in the film by film coating or the like, in granules by granulation or the like, in the matrix (for example, around polyethylene oxide), or the like.

Examples of the disintegrating agent include corn starch, potato starch, carmellose calcium, carmellose sodium, and low-substituted hydroxypropylcellulose.

Examples of the acidulant include citric acid, tartaric acid, and malic acid.

Examples of the effervescent agent include sodium bicarbonate.

Examples of the artificial sweetener include saccharin sodium, dipotassium glycyrrhizinate, aspartame, stevia, and thaumatin.

Examples of the flavor include lemon, lemon-lime, orange, and menthol.

Examples of the lubricant include magnesium stearate, calcium stearate, sucrose fatty acid esters, polyethylene glycol, talc, and stearic acid.

Examples of the coloring agent include food yellow No. 4, food yellow No. 5, food red No. 3, food red No. 102, and food blue No. 3.

Examples of the buffer include citric acid, succinic acid, fumaric acid, tartaric acid, ascorbic acid, and salts thereof; glutamic acid, glutamine, glycine, aspartic acid, alanine, arginine, and salts thereof; and magnesium oxide, zinc oxide, magnesium hydroxide, phosphoric acid, boric acid, and salts thereof.

Examples of the antioxidant include ascorbic acid, dibutyl hydroxytoluene, and propyl gallate.

Examples of the surfactant include polysorbate 80, sodium laurylsulfate, and polyoxyethylene hydrogenated castor oil.

These pharmaceutical additives may be appropriately added alone, or as a combination of two or more thereof, in an appropriate amount.

Each pharmaceutical additive may be contained in an amount such that the desired effects of the present invention may be achieved.

Examples of the pharmaceutical composition (formulation) of the present invention include tablets prepared by a known method per se, for example, multi-layered tablets, such as a bi-layered tablet in which the modified release portion and the immediate release portion are laminated, a multi-layered tablet in which a plurality of the modified release portions and the immediate release portions are laminated, and a three-layered tablet in which a drug-free layer of a hydrophilic substance and/or a water-insoluble substance is sandwiched between the modified release portion and the immediate release portion; a dry-coated tablet having the modified release portion as an internal core and the immediate release portion as an outer core; and a film-coated tablet in which the modified release portion as a core is coated with the immediate release portion by film coating.

Hereinafter the process of manufacturing the pharmaceutical composition of the present invention will be explained in detail.

(1) Pulverizing and Mixing Steps

An apparatus and a method used in the pulverizing step are not particularly limited, so long as drugs and appropriate additives can be pharmaceutically pulverized. Examples of the apparatus include a hammer mill, a ball mill, a jet mill, and a colloid mill. The conditions for pulverization may be appropriately selected and are not particularly limited.

An apparatus and a method used in the mixing step subsequent to the pulverizing step are not particularly limited, so long as components can be uniformly mixed pharmaceutically.

(2) Modified Release Portion: Granulation Step

An apparatus and a method used in this step are not particularly limited, so long as the hydrogel-forming polymer can be granulated using a spray liquid.

Examples of granulation include a high-speed agitation granulation method, a pulverization granulation method, a fluidized bed granulation method, an extrusion granulation method, a tumbling granulation method, and a spray granulation method; and apparatuses used in these methods. A fluidized bed granulation method and apparatus may be used in another embodiment, and a tumbling fluidized bed granulation method and apparatus may be used in still another embodiment. The resulting granulated product may be dried. The drying method is not particularly limited, so long as the granulated product can be pharmaceutically dried.

(3) Immediate Release Portion: Granulation Step

An apparatus and a method used in this step are not particularly limited, so long as the drugs can be granulated using a spray liquid.

Examples of granulation include a fluidized bed granulation method, a melting granulation, a high-speed agitation granulation method, a pulverization granulation method, an extrusion granulation method, a tumbling granulation method, a spray granulation method, and a dry granulation method; and apparatuses used in these methods. A fluidized bed granulation method may be used in another embodiment.

As a binder used in the wet granulation, a hydrophilic substance is preferable and, for example, polyethylene glycol, maltose, or polyvinylpyrrolidone may be used. These binders may be used alone, or as an appropriate combination of two or more thereof.

The conditions for preparing the spray liquid may be appropriately selected and are not particularly limited.

The resulting granulated product may be dried. The drying method is not particularly limited, so long as the granulated product can be pharmaceutically dried.

(4) Forming Step

An apparatus and a method used in this step are not particularly limited, so long as the pharmaceutical composition of the present invention can be formed. Examples of the method include:
a method in which the drugs and appropriate additives are mixed without granulation and drying, and directly compression-molded to obtain tablets;
a method in which the granulation step is carried out, a lubricant is added to the resulting granulated product, and the mixture is compression-molded to obtain tablets;
a method of preparing bi-layered tablets by laminating the modified release portion and the immediate release portion;
a method of preparing multi-layered tablets by laminating a plurality of the modified release portions and the immediate release portions;
a method of preparing multi-layered tablets by adding a drug-free layer between the modified release portion and the immediate release portion; and
a method of preparing dry-coated tablets having the modified release portion as an internal core and the immediate release portion as an outer core. A method of preparing bi-layered tablets may be used in another embodiment.

Examples of a tabletting machine include a multilayered rotary tabletting machine and an oil press.

The conditions for tabletting such as a tabletting pressure are not particularly limited, so long as bi-layered tablets and multi-layered tablets can be prepared. When bi-layered tablets are prepared, a granulated product for the first layer and another granulated product for the second layer are laminated, and compressed under a tabletting pressure of approximately 2 kN to approximately 20 kN to prepare the bi-layered tablets. In another embodiment, a granulated product for the first layer is compressed under a tabletting pressure of approximately 0.1 kN to approximately 10 kN, and another granulated product for the second layer is placed on the first layer and compressed under a tabletting pressure of approximately 2 kN to approximately 20 kN to prepare the bi-layered tablets. When multi-layered tablets are prepared, a tabletting pressure can be appropriately adjusted to carry out the compression.

The hardness of the resulting tablet is not particularly limited, so long as the tablet is not damaged during the manufacturing and distribution process. The hardness may be, for example, 2 to 20 N.

(5) Film Coating

After the tabletting, the obtained tablets may be film coated.

The method of film coating is not particularly limited, so long as the tablets can be pharmaceutically coated. Examples of the coating include pan coating and dip coating.

Film coating agents may be added alone, or as a combination of two or more thereof, in an appropriate amount. The rate of coating is not particularly limited, so long as a film can be formed. The coating rate is, for example, 1% to 10%.

When a core as the modified release portion is coated with the immediate release portion to prepare film coated tablets, a spray liquid prepared by dissolving or dispersing the components of the immediate release portion in a solvent such as water may be sprayed on the core to obtain the film coated tablets. The coating rate is not particularly limited, so long as the film of the immediate release portion can be formed. The coating rate is, for example, 1% to 20%.

After the film coating, the resulting film coated tablets may be dried. The drying method is not particularly limited, so long as the film coated tablets can be pharmaceutically dried. The conditions for drying are not particularly limited, so long as they are appropriately selected in view of, for example, the stability of the formulation. The initial water content after film coating is preferably 0.1% to 2% in accordance with, for example, the stability.

The pharmaceutical composition for oral administration of the present invention may be used as a pharmaceutical composition for treating lower urinary tract symptoms associated with benign prostatic hyperplasia.

The process of manufacturing the pharmaceutical composition of the present invention is not particularly limited, so long as a desired pharmaceutical formulation can be produced by appropriately combining the methods described above, or known methods per se.

EXAMPLES

The present invention will be further illustrated by, but is by no means limited to, the following Examples, Comparative Examples, and Experimental Examples.

Example 1

(1) Preparation of Mixed Powder for Modified Release Portion

A spray liquid was prepared by dissolving 1.2 parts of macrogol 8000 in 4.8 parts of water while stirring, and suspending 0.1 parts of previously pulverized tamsulosin hydrochloride in this solution. Into a fluidized bed granulating apparatus, 8.8 parts of macrogol 8000 and 50 parts of PEO [POLYOX (registered trademark) WSR-303, manufactured by Dow] were loaded, and granulated by spraying the spray liquid. The resulting granulated product was dried, and 60.1 parts of the dried granulated product was mixed with 0.3 parts of magnesium stearate to prepare mixed powder for a modified release portion.

(2) Preparation of Mixed Powder for Immediate Release Portion

A spray liquid was prepared by dissolving 1 part of maltose in 4 parts of water while stirring. After 0.6 parts of solifenacin succinate and 2.4 parts of mannitol were mixed and pulverized, the resulting pulverized mixture and 5.9 parts of mannitol were loaded into a fluidized bed granulating apparatus, and granulated by spraying the spray liquid. The resulting granulated product was dried, and 9.9 parts of the dried granulated product was mixed with 0.1 parts of magnesium stearate to prepare mixed powder for an immediate release portion.

(3) Tabletting and Coating

The resulting mixed powder for a modified release portion and the resulting mixed powder for an immediate release portion were formed into tablets using a multilayered rotary tabletting machine to obtain a formulation (bi-layered tablets) of the present invention. The resulting bi-layered tablets were spray-coated with a spray liquid previously prepared by dissolving and dispersing 5.04 parts of hydroxypropylmethylcellulose, 0.95 parts of macrogol 6000, and 1.26 parts of yellow ferric oxide to obtain a pharmaceutical composition (film-coated tablets) of the present invention.

Experimental Example 1

The pharmaceutical composition prepared in Example 1 was subjected to a dissolution test carried out in accordance with a dissolution test, method 2 (paddle method, 50 rpm) described in the Japanese Pharmacopoeia. The volume of a test fluid was 900 mL. The percentages of solifenacin dissolution after 15 minutes, 30 minutes, and 60 minutes from the beginning of the test are shown in Table 1.

Example 2

(1) Preparation of Mixed Powder for Modified Release Portion

A spray liquid was prepared by dissolving 1.2 parts of macrogol 8000 in 4.8 parts of water while stirring, and suspending 0.1 parts of previously pulverized tamsulosin hydrochloride in this solution. Into a fluidized bed granulating apparatus, 8.8 parts of macrogol 8000 and 50 parts of PEO [POLYOX (registered trademark) WSR-303, manufactured by Dow] were loaded, and granulated by spraying the spray liquid. The resulting granulated product was dried, and 60.1 parts of the dried granulated product was mixed with 0.3 parts of magnesium stearate to prepare mixed powder for a modified release portion.

(2) Preparation of Mixed Powder for Immediate Release Portion

After 0.6 parts of solifenacin succinate and 2.4 parts of mannitol were mixed and pulverized, the resulting pulverized mixture, 5.9 parts of mannitol, 1 part of PEG 8000, and 0.1 parts of magnesium stearate were mixed to prepare mixed powder for an immediate release portion.

(3) Tabletting

The resulting mixed powder for a modified release portion and the resulting mixed powder for an immediate release portion were formed into tablets using an oil press to obtain a pharmaceutical composition (bi-layered tablets) of the present invention.

Example 3

(1) Preparation of Mixed Powder for Modified Release Portion

A spray liquid was prepared by dissolving 1.2 parts of macrogol 8000 in 4.8 parts of water while stirring, and suspending 0.1 parts of previously pulverized tamsulosin hydrochloride in this solution. Into a fluidized bed granulating apparatus, 8.8 parts of macrogol 8000 and 50 parts of PEO [POLYOX (registered trademark) WSR-303, manufactured by Dow] were loaded, and granulated by spraying the spray liquid. The resulting granulated product was dried, and 60.1 parts of the dried granulated product was mixed with 0.3 parts of magnesium stearate to prepare mixed powder for a modified release portion.

(2) Preparation of Mixed Powder for Immediate Release Portion

A spray liquid was prepared by dissolving 0.5 parts of polyvinylpyrrolidone (PVP K90) in 4 parts of water while stirring. After 0.6 parts of solifenacin succinate and 2.4 parts of mannitol were mixed and pulverized, the resulting pulverized mixture and 6.4 parts of mannitol were loaded into a fluidized bed granulating apparatus, and granulated by spraying the spray liquid. The resulting granulated product was dried, and 9.9 parts of the dried granulated product was mixed with 0.1 parts of magnesium stearate to prepare mixed powder for an immediate release portion.

(3) Tabletting

The resulting mixed powder for a modified release portion and the resulting mixed powder for an immediate release portion were formed into tablets using a multilayered rotary tabletting machine to obtain a pharmaceutical composition (bi-layered tablets) of the present invention.

Comparative Example 1

(1) Preparation of Mixed Powder for Modified Release Portion

A spray liquid was prepared by dissolving 1.2 parts of macrogol 8000 in 4.8 parts of water while stirring, and suspending 0.1 parts of previously pulverized tamsulosin hydrochloride in this solution. Into a fluidized bed granulating apparatus, 8.8 parts of macrogol 8000 and 50 parts of PEO [POLYOX (registered trademark) WSR-303, manufactured by Dow] were loaded, and granulated by spraying the spray liquid. The resulting granulated product was dried, and 60.1 parts of the dried granulated product was mixed with 0.3 parts of magnesium stearate to prepare mixed powder for a modified release portion.

(2) Preparation of Mixed Powder for Immediate Release Portion

A spray liquid was prepared by dissolving 204 parts of hydroxypropylmethylcellulose 2910 in 1,836 parts of water while stirring. After 340 parts of solifenacin succinate and 1,360 parts of lactose were mixed and pulverized, the resulting pulverized mixture, 2,125 parts of lactose, and 1,020 parts of corn starch were loaded into a fluidized bed granulating apparatus, and granulated by spraying the spray liquid. The resulting granulated product was dried, and 1,188 parts of the dried granulated product was mixed with 12 parts of magnesium stearate to prepare mixed powder for an immediate release portion.

(3) Tabletting

The resulting mixed powder for a modified release portion and the resulting mixed powder for an immediate release portion were formed into tablets using an oil press to obtain a pharmaceutical composition (bi-layered tablets) for comparison.

Experimental Example 2

The pharmaceutical compositions prepared in Examples 1 to 3 and Comparative Example 1 were subjected to a dissolution test carried out in accordance with a dissolution test, method 1 (basket method, 100 rpm) described in the Japanese Pharmacopoeia. The volume of a test fluid was 900 mL. The dissolution rates of solifenacin after 15 minutes, 30 minutes, and 60 minutes from the beginning of the test are shown in Table 2.

TABLE 1

|  | 15 min. | 30 min. | 60 min. |
| --- | --- | --- | --- |
| Example 1 | 71% | 85% | 94% |

TABLE 2

|  | 15 min. | 30 min. | 60 min. |
| --- | --- | --- | --- |
| Example 1 | 93% | 95% | 96% |
| Example 2 | 96% | 98% | 99% |
| Example 3 | 94% | 96% | 97% |
| Comparative Example 1 | 62% | 82% | 88% |

INDUSTRIAL APPLICABILITY

The present invention provides a pharmaceutical composition for oral administration comprising a modified release portion containing tamsulosin or a pharmaceutically acceptable salt thereof, and an immediate release portion containing solifenacin or a pharmaceutically acceptable salt thereof. The pharmaceutical composition of the present invention exhibits a release rate similar to those of the current single drug formulations, and thus, can be used as a formulation technique which provides a single formulation (i.e., a combined formulation) capable of expecting pharmacological effects equivalent to those of the current single drug formulations.

As above, the present invention was explained with reference to particular embodiments, but modifications and improvements obvious to those skilled in the art are included in the scope of the present invention.

The invention claimed is:

1. A pharmaceutical composition for oral administration, comprising:
   (1) a modified release layer comprising tamsulosin or a pharmaceutically acceptable salt thereof, wherein the modified release layer contains a polymer which forms a hydrogel, and
   (2) an immediate release layer comprising solifenacin or a pharmaceutically acceptable salt thereof and a hydrophilic substance, wherein the hydrophilic substance is one compound, or two compounds selected from the group consisting of maltose and mannitol, and wherein 70% or more of solifenacin is dissolved in 15 minutes, wherein the pharmaceutical composition is in a bi-layered tablet form.

2. The pharmaceutical composition for oral administration according to claim 1, wherein the immediate release layer is disintegrated and/or dissolved before the modified release layer forms a gel.

3. The pharmaceutical composition for oral administration according to claim 1, wherein 90% or more of solifenacin is dissolved in 60 minutes.

4. The pharmaceutical composition for oral administration according to claim 1, wherein 85% or more of solifenacin is dissolved in 30 minutes and 90% or more of solifenacin is dissolved in 60 minutes.

5. The pharmaceutical composition for oral administration according to claim 1, wherein the hydrophilic substance accounts for 5% by weight to 99% by weight.

6. The pharmaceutical composition for oral administration according to claim 1, wherein maltose as the hydrophilic substance is used as a binder.

7. The pharmaceutical composition for oral administration according to claim 1, wherein mannitol as the hydrophilic substance is used as a filler.

8. The pharmaceutical composition for oral administration according to claim 1, wherein the hydrogel-forming polymer has a viscosity of 4000 mPa·s or more in a 1% aqueous solution (25° C.).

9. The pharmaceutical composition for oral administration according to claim 8, wherein the hydrogel-forming polymer is one polymer or two or more polymers selected from the group consisting of polyethylene oxide, hydroxypropylmethylcellulose, carboxymethylcellulose sodium, and a carboxyvinyl polymer.

10. The pharmaceutical composition for oral administration according to claim 9, wherein the hydrogel-forming polymer is polyethylene oxide.

11. The pharmaceutical composition for oral administration according to claim 10, wherein polyethylene oxide has a viscosity-average molecular weight of 5,000,000 or more.

12. The pharmaceutical composition for oral administration according to claim 1, wherein the hydrogel-forming polymer accounts for 5% by weight to 95% by weight.

13. The pharmaceutical composition for oral administration according to claim 1, wherein the modified release layer further contains an additive which allows water to penetrate into the formulation.

14. The pharmaceutical composition for oral administration according to claim 13, wherein the additive which allows water to penetrate into the formulation has a solubility such that the amount of water necessary to dissolve 1 g of the additive is 5 mL or less.

15. The pharmaceutical composition for oral administration according to claim 14, wherein the additive which allows water to penetrate into the formulation accounts for 3% by weight to 80% by weight.

16. The pharmaceutical composition for oral administration according to claim 1, which is a pharmaceutical composition for treating lower urinary tract symptoms associated with benign prostatic hyperplasia.

* * * * *